United States Patent
Ytteborg

(10) Patent No.: US 7,101,350 B2
(45) Date of Patent: Sep. 5, 2006

(54) BREAST CUP AND METHOD OF MANUFACTURING A BREAST CUP, AND ALSO USE OF THIS

(75) Inventor: Tone Fleischer Ytteborg, Oslo (NO)

(73) Assignee: Mamma Lactans AS, Olso (NO)

( * ) Notice: Subject to any disclaimer, the term of this patent is extended or adjusted under 35 U.S.C. 154(b) by 169 days.

(21) Appl. No.: 10/220,034

(22) PCT Filed: Jun. 18, 2002

(86) PCT No.: PCT/NO02/00216

§ 371 (c)(1),
(2), (4) Date: Feb. 5, 2003

(87) PCT Pub. No.: WO02/102439

PCT Pub. Date: Dec. 27, 2002

(65) Prior Publication Data

US 2003/0153869 A1 Aug. 14, 2003

(30) Foreign Application Priority Data

Jun. 18, 2001 (NO) .......................... 20013023

(51) Int. Cl.
*A61M 1/06* (2006.01)

(52) U.S. Cl. ........................................ 604/74
(58) Field of Classification Search ............... 604/35, 604/36, 73–76, 132, 133, 346
See application file for complete search history.

(56) References Cited

U.S. PATENT DOCUMENTS

| | | | |
|---|---|---|---|
| 4,263,912 A | 4/1981 | Adams | |
| 4,680,028 A | 7/1987 | Stuart | |
| 4,964,851 A | 10/1990 | Larsson | |
| 5,049,126 A | 9/1991 | Larsson | |
| 5,885,246 A | * 3/1999 | Ford | .............. 604/74 |
| 6,663,587 B1 | 12/2003 | Silver et al. | |

FOREIGN PATENT DOCUMENTS

| | | |
|---|---|---|
| DE | 4102634 | 8/1992 |
| EP | 0 727 234 A1 | 8/1996 |
| EP | 1 034 807 A1 | 9/2000 |
| EP | 1034807 * | 9/2000 |
| FR | 1.067.421 | 6/1954 |
| NO | 307079 | 2/2000 |
| SU | 1745262 | 7/1992 |
| WO | WO 92/07593 | 5/1992 |
| WO | WO 98/22160 A1 | 5/1998 |
| WO | WO 99/44650 A1 | 9/1999 |
| WO | WO 00/10625 A1 | 3/2000 |

OTHER PUBLICATIONS

Ford, D. R.; "Breast Pump Insert"; EPO 072734, Abstract Only; Aug. 21, 1996.
Grant, E. M.; "Portable Electric Breast Pump"; EPO 198469, Abstract Only; Oct. 22, 1986.

* cited by examiner

*Primary Examiner*—Manuel Mendez
(74) *Attorney, Agent, or Firm*—Browdy and Neimark, PLLC

(57) ABSTRACT

Breast cup for placing on a woman's breast, which breast cup includes an outer part (1) and an inner part (2), which inner part (2) includes an approximately cylindrical portion (11) with one or more areas provided with flexible membranes (13), as well as an approximately conical portion (12) with one or more areas provided with flexible membranes (14), which outer portion (1) includes a generally conical portion (5) shaped to be complementary to the conical portion (12) of the inner part (2), a generally cylindrical portion (4) shaped to be complementary to the cylindrical portion (11) of the inner part (2).

The invention also comprises a method of manufacturing the breast cup, as well as a method of using the breast cup.

6 Claims, 7 Drawing Sheets

BREAST CUP AND METHOD OF MANUFACTURING A BREAST CUP, AND ALSO USE OF THIS

The present invention regards a breast cup, a method of manufacture for the breast cup, and use of this in accordance with the preamble of the independent claims.

Over the last few years, the number of women who breastfeed their children has been increasing steadily. From a nutritional and psychological standpoint, this is considered to be the best thing for both mother and child.

The most common way of giving the child breast milk is to let the child suck directly from the breast. However, in certain cases it is not practical or possible to let the child suck directly from the breast. Examples of such cases may be:

when the child is premature and is not able to suck,
when the mother has too little milk,
when the mother is ill and requires a stronger stimulus,
medically indicated mastitis, where the mother can not, as a consequence of the treatment, give the milk to the child, and where the breast must be emptied.

For purely practical reasons, it may also be appropriate for others to have the possibility of feeding the child.

A number of physiological and psychological factors influence, and may stop, the milk production. One important factor is the stimulation of the breast in order to start the milk production. The stimulation of the breast includes a total of three components that must be present for the milk production to start:

Stimulation of the actual breast, where the greatest stimulus is by the edges of the areola. Here are the so-called "milk lakes", which when pressured will release Oxytocin from the hypophysis. This hormone acts directly on the milk ducts, so that they dilate and open up to be emptied. This happens when the child grips the breast by opening its mouth widely. The jaws and lips will then stimulate the areola, which is situated approximately 2.5–3 cm from the base of the nipple.

Stimulation of the actual nipple, through squeezing and massaging. This occurs when the child's tongue and palate envelops the nipple. Tactile stimulation entails a strong stimulus, and thereby hormonal response. The actual sucking, which takes place when the child sucks.

A number of different breast cups and associated breast pumps have been developed, which to some extent stimulate some of the above factors.

Besides the breast pump having to be able to stimulate these factors, it must also be comfortable in use, soft and able to adapt to the various shapes and sizes of the breast. At the same time, it should be easy to use.

A number of different breast pumps are known, which consist of a cup or similar that is placed over the breast, a manual or mechanical vacuum pump connected to the cup, which creates an intermittent vacuum in the cup, and a receptacle for the expressed milk. The expressed milk typically flows from the cup and into a receptacle for storage and subsequent use.

From SU-A-1 745 262 A1 there is known a breastfeeding device consisting of an outer housing made from reinforced latex, an inflatable element in the form of concentric latex tubes and a milk receptacle connected to a milk tube. Each of the concentric latex tubes of the inflatable element are connected to a pressure source via supply lines and an air line. Consequently the device consists of concentric inflatable rings arranged around the breast. In this publication, there is neither an illustration nor a description of these rings being individually inflatable, nor is there an illustration or description of the creation of a pulsating wave directed at the nipple.

From U.S. Pat. No. 5,049,126 there is known an insert for a breast cup for a breast pump, the purpose of which is to achieve a more realistic simulation of a baby pressing against and massaging the nipple. The insert consists of a funnel-shaped portion in the form of a truncated cone with a tubular portion provided by the part of the funnel-shaped portion exhibiting the smallest diameter. In the tubular portion there is provided at least one elongated opening located over the point where the actual nipple will be when the device is used. This elongated opening in the tubular portion is provided with a flexible membrane. Upon a vacuum pump creating a negative pressure in the insert, the flexible membrane will be sucked into the insert, carefully squeezing and massaging the nipple in order to promote the milk production. This insert will stimulate neither the rest of the breast nor the area around the actual nipple. The actual funnel-shaped portion seems, in accordance with the specification, to be manufactured from a rigid material, thus making the insert difficult to adapt to different shapes and sizes of breasts. As the insert is rigid, it may cause a certain amount of discomfort. In addition, the insert is intended to be placed in the breast cup of an existing breast pump.

From U.S. Pat. No. 4,680,028 there is known a breast cup for a breast pump, which breast cup is manufactured from a transparent, flexible material such as silicone rubber. The breast cup is in the form of a funnel-shaped portion with a tubular extension. In the transition zone between the funnel-shaped portion and the tubular portion, the wall thickness is reduced for the purpose of massaging the nipple and the surrounding area as a result of the suction created by a vacuum pump. An area of the funnel-shaped portion having the largest diameter has also been given a reduced wall thickness, so that the woman's fingers may massage the remaining parts of the breast located under this area.

EP-198 469 describes a breast pump, including a vacuum pump. The breast cup of the apparatus consists of parts that are to simulate the mouth, throat and jaws of the child. The breast cup grips around the breast at a pressure created by the pump. An opening valve controls the pressure. In use, the woman may massage the breast and control the rhythm herself.

WO-92/07593 describes an elastomer insert for a breast cup for a breast pump, which insert contains depressions and grooves in order to be more adaptable to the breast. The insert consists of a funnel-shaped portion in the form of a truncated cone and a tubular portion connected to the part of the funnel-shaped portion having the smallest diameter. On the outside of the funnel-shaped portion are provided oval and curved cut-outs, so that a thin membrane is formed in the insert in the area around the nipple. The purpose of this is, according to the specification, to prolong the duration of the suction created by the pump stroke, so as to increase the milk production and make the insert softer and more comfortable for the user. This insert will not be able to provide the desired stimulus for the actual nipple, nor for the rest of the breast. In addition, this insert is intended to be placed in an existing breast cup of a breast pump.

From U.S. Pat. No. 4,964,851 there is known an electrically driven breast pump consisting of a breast cup made from a partly flexible material, a suction pump and a rotating valve. The rotating valve alternates the direction of suction from the pump between the breast cup and the receptacle, so as to create a reciprocal suction effect on the breast.

From EP-727 234 there is known an insert for a funnel-shaped breast cup. The insert is provided with portions of reduced thickness, to allow these portions to move against the inside of the funnel-shaped breast cup and thereby provide a certain stimulation of the areola area upon a vacuum being created in the breast cup. However, the vacuum and the frequency that provides this stimulation are not independently adjustable, and as such it will not be possible to create a "pulsating wave" from the breast towards the actual nipple. Thus it may be difficult to achieve the desired degree of stimulation, and a strong vacuum may at worst cause an obstructing squeeze against the milk ducts, thereby preventing the milk from being expressed.

DE 4 102 634 A1 describes a breast cup in the form of an inflatable hollow body enclosing the breast. Both the cavity of the breast cup and the opening of the breast cup located by the nipple are connected to a vacuum pump. There is however no description or illustration of any separate adjustment of the pressure and frequency of the vacuum pump.

A common feature of all the breast cups and breast pumps described in the above publications is that they only have an adjustable vacuum, but not an adjustable or pulsating pressure that stimulates the area immediately surrounding the areola. Thus none of these devices are capable of mimicking the effect that arises from a child sucking at the breast.

A great disadvantage of the above described solutions is the lack of stimulation of the area of the breast located by and outside the areola. Most of the above described solutions only stimulate the actual nipple and the area of the breast located immediately around the actual nipple. Such stimulation is not sufficient to initiate a satisfactory milk production. The area of the breast situated at a distance of approximately 2.5 to 3 cm from the base of the nipple, the areola, holds a number of so-called "milk lakes", which upon stimulation will open the milk-producing glands. This is the area that is stimulated by the child's lips during breastfeeding, and which gives a hormonal response in the form of Oxytocin.

Another disadvantage of the previously known solutions is that they require a relatively strong vacuum in order to achieve the intended effect. This is highly uncomfortable to the user, and may cause pain.

Yet another disadvantage of several of the devices discussed above is the fact that they are made from relatively inflexible materials, which are not sufficiently adaptable to the shape of the breast. This may cause the user discomfort.

A further disadvantage of the previously known solutions is the fact that these require a relatively strong, constant vacuum. If the vacuum is reduced, the expression of milk will decrease, as the vacuum is the only stimulus for expression. Using a relatively strong vacuum as the sole stimulus may cause pain and discomfort to the user.

From the Applicant's own Norwegian patent 307079 there is known a breastfeeding device of the type mentioned by way of introduction, which solves most of the problems of the above described solutions. The breastfeeding device in accordance with this patent includes a breast cup consisting of a total of three stimulating means, i.e. a first stimulating means for stimulation of the actual nipple. This first stimulating means is connected to a vacuum source having an adjustable vacuum and frequency. Further, the device includes a second and third stimulating means in the form of inflatable pads or cavities in the breast cup, which second and third stimulating means are connected to a pressure source having separately adjustable pressure and frequency. Having a total of three different stimulating means with individual adjustment entails a somewhat complex and costly control mechanism.

The above mentioned purposes and advantages are achieved in accordance with the invention by a breast cup for positioning around a nipple and an areola area on a woman's breasts, which breast cup is in the form of a truncated cone with an approximately cylindrical portion by the truncated part of the cone, which cylindrical portion forms a first and second stimulating means that simulate the suction and the palate/tongue of a breastfeeding child, respectively, and the conical part of the breast cup forms a third stimulating means that simulates the lips/jaws of a breastfeeding child, characterised in that the breast cup includes an outer part and an inner part, which inner part includes an approximately cylindrical portion having one or more areas provided with flexible membranes, as well as an approximately conical portion having one or more areas provided with flexible membranes, which outer part includes a generally conical portion shaped so as to complement the conical portion of the inner part, a generally cylindrical portion shaped so as to complement the cylindrical portion of the inner part.

Preferably, the inner part or the outer part are provided with an additional portion in the form of an extension of the approximately cylindrical portion, which additional portion is provided with connecting means for connecting the breast cup to a milk collecting device.

Preferably, the outer part and the inner part are manufactured from a polymer material approved for medical use, preferably a thermoplastic such as polypropylene.

The flexible membranes are manufactured from a polymer material approved for medical use, preferably a thermoplastic elastomer compatible with the polymer material of the inner and outer parts.

The invention also regards a method of manufacturing a breast cup for positioning around a nipple and an areola area of a woman's breast, which breast cup is in the form of a truncated cone with an approximately cylindrical portion by the truncated part of the cone, which cylindrical portion of the breast cup forms first and second stimulating means that simulate the suction and the lips of a breastfeeding child, respectively, and the conical part of the breast cup forms a third stimulating means simulating the palate of a breastfeeding child, which breast cup includes an outer part and an inner part, which method comprises the following steps:

(a) separate manufacture of the inner part and the outer part, preferably by injection moulding of a thermoplastic material;

(b) providing membranes on the inner part, preferably by hot welding, (c) heating portions of the outside of the inner part and the inside of the outer part, (d) pressing the inner part and the outer part together.

Preferably, the method also includes the simultaneous heating of portions of the outside of the inner part and the inside of the outer part by means of a complementary shaped heated plate.

The invention also regards a method of pumping breast milk by means of the above described breast cup, characterised in that the method comprises the following steps:

a) connecting the first stimulating means to a vacuum source with an adjustable pressure and frequency;

b) connecting the second and third stimulating means to one or more pressure sources with individually adjustable pressures and frequencies, c) applying a pulsating vacuum of the order of 50 mbar to the first stimulating means for approximately 20 seconds, d) increasing the vacuum in point c) to 100–150 mbar for the next 10 seconds while at the same time applying a pulsating pressure in the order of 50 to 450 mbar to the second stimulating means, e) reducing the pressure of the second stimulating means while at the same time applying a pulsating pressure in the order of 300–500 mbar to the third stimulating means, f) reducing the vacuum of the first stimulating means, g) adjusting the pressure to the second and third stimulating means separately approximately 30 seconds after point c) has been carried out.

In the following, the invention will be explained in greater detail by means of examples of embodiments, with reference to the accompanying drawings, in which.

Figure 5:
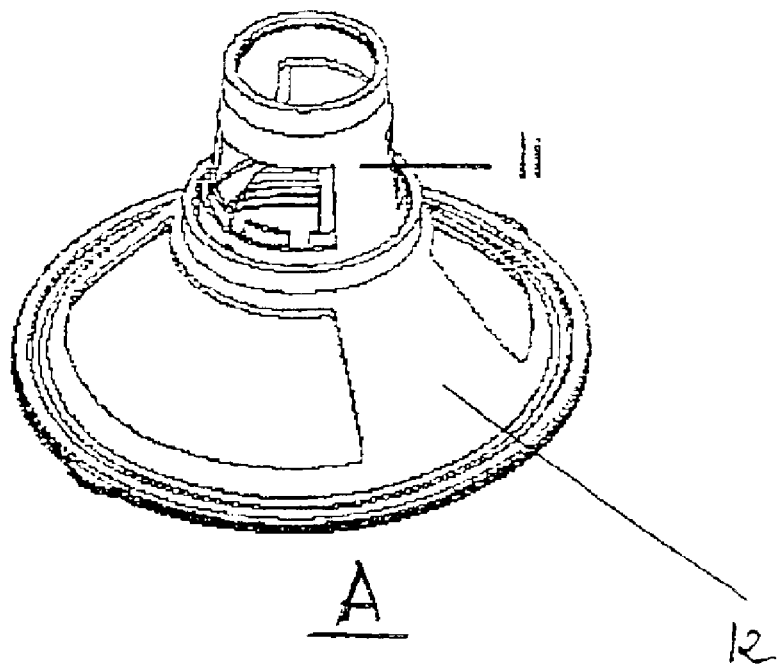
Figure 5:
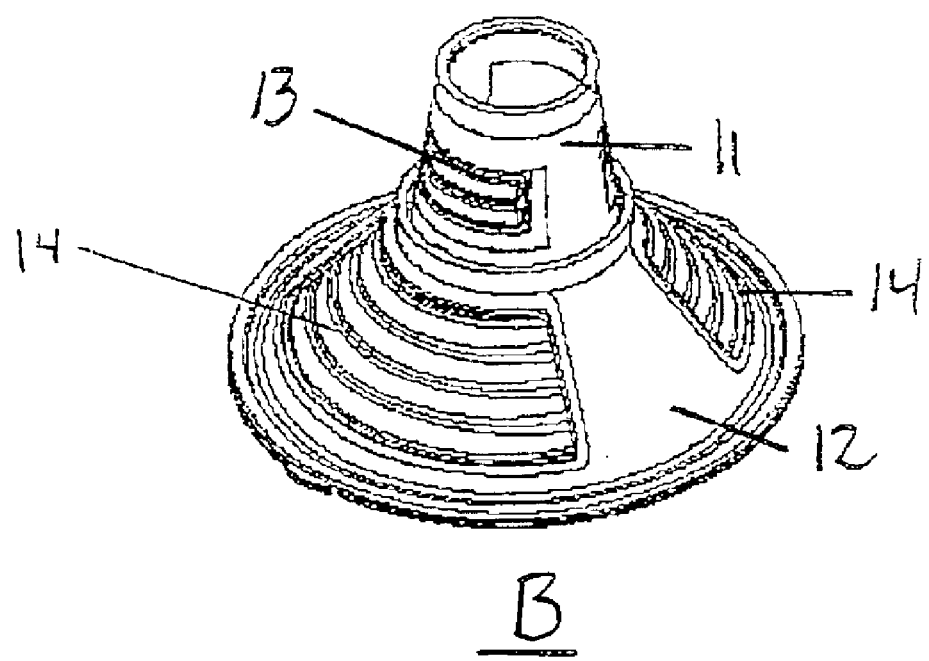
Figure 6:
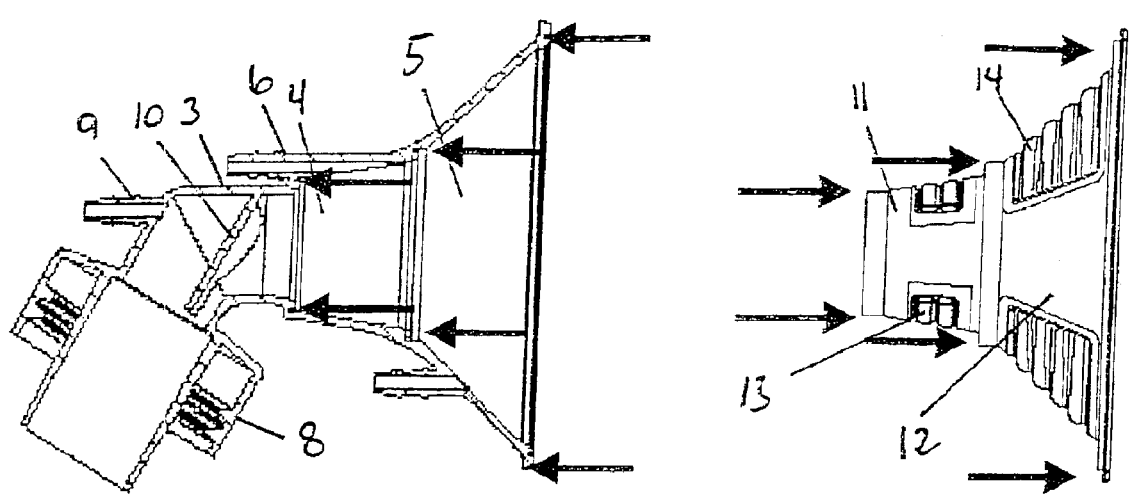
Figure 7:
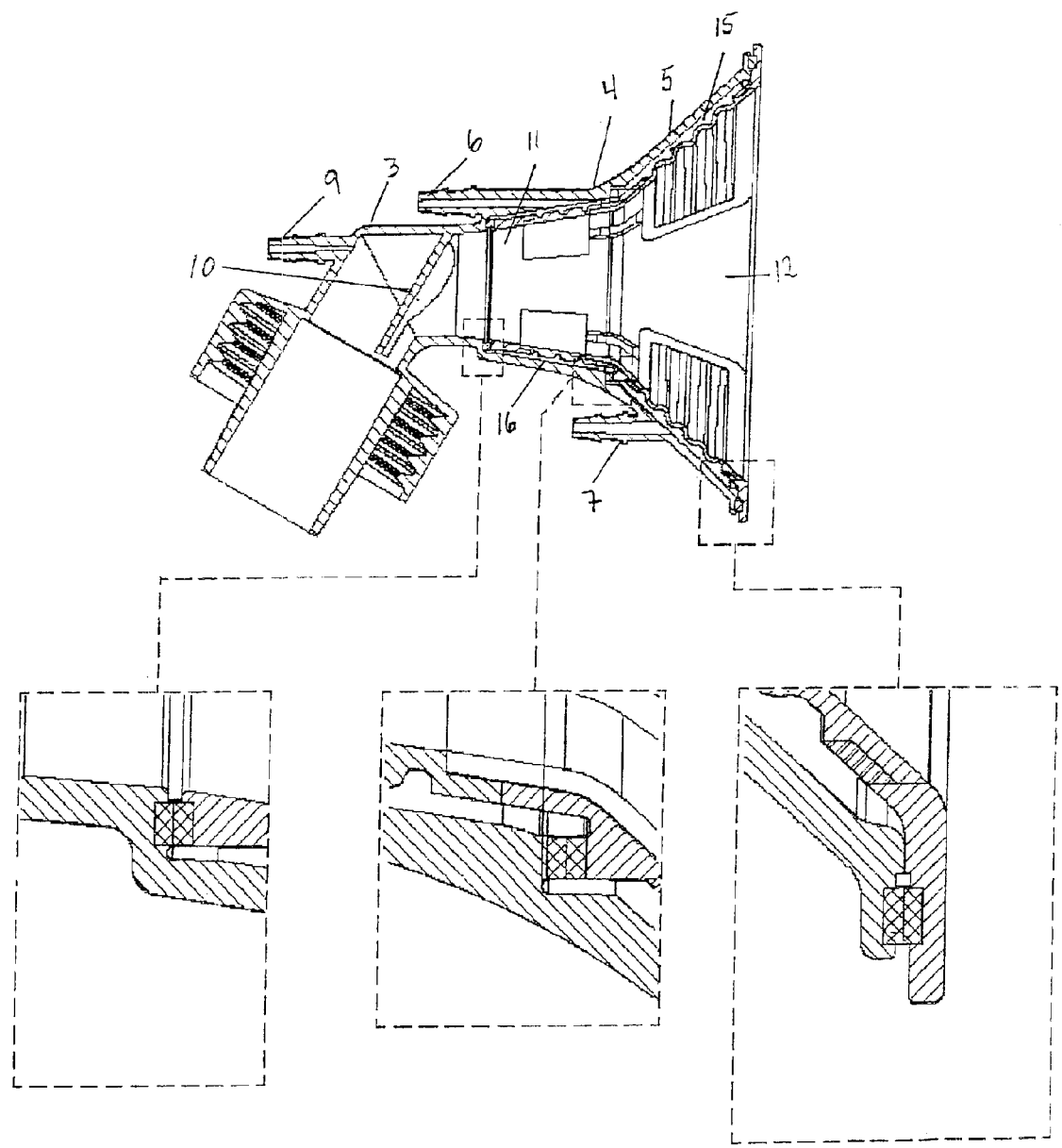

FIGS. 3a and b are top and perspective views, respectively, of an embodiment of the inner part of the breast cup;

FIGS. 4a and b are top and perspective views, respectively, of a second embodiment of the inner part of the breast cup;

FIGS. 5–7 illustrate various steps of a preferred method of manufacturing the breast cup in accordance with the present invention.

Figure 8:
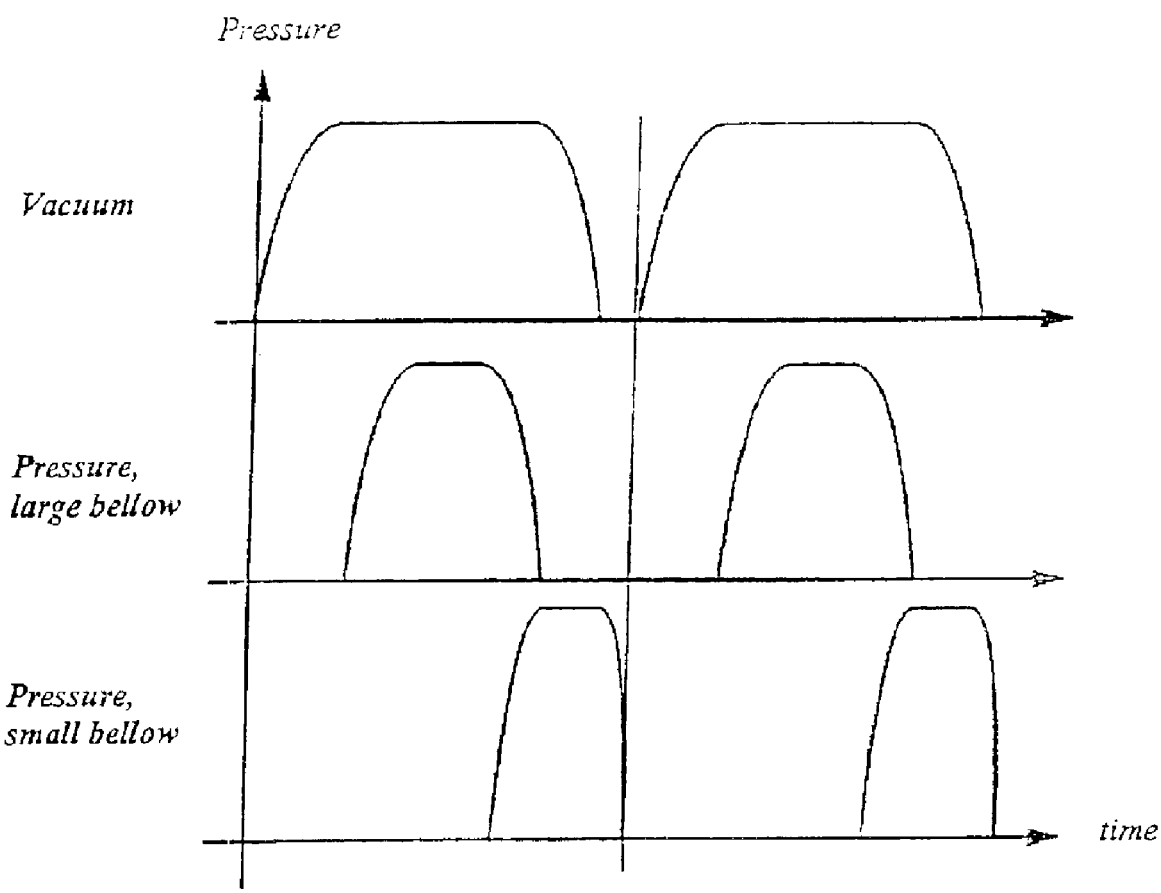

FIG. 8 is a figure showing pressure and vacuum conditions, respectively, as functions of time when using the breast cup.

Figure 1:
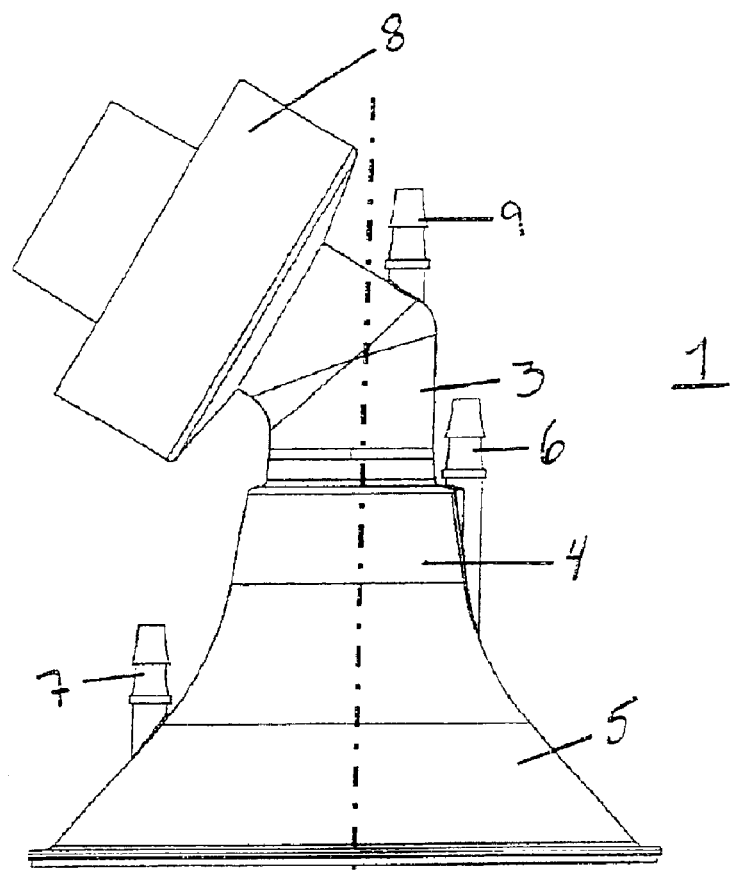
FIG. 1 is a side view of an inner part of the breast cup in accordance with the invention.
Figure 2:
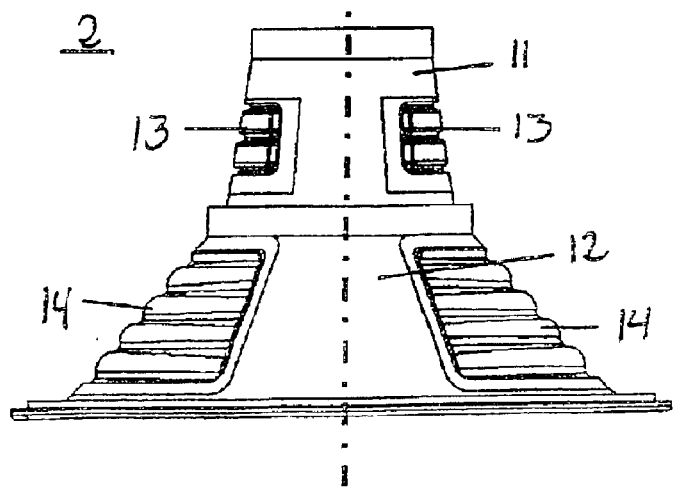
FIG. 2 is a side view of an outer part of the breast cup in accordance with the invention.

FIGS. 1 and 2 show an embodiment of a breast cup in accordance with the invention. The breast cup consists of an outer part 1 and an inner part 2. FIG. 1 is a side view of the outer part 1 of the breast cup. The outer part 1 consists of a first portion 3 designed to be connected to a collecting device for the milk (not shown), a second portion 4, e.g. in the form of a cylinder or a truncated cone, and a third portion 5, preferably in the form of a truncated cone. The second and third portions 4, 5 are each provided with means of connecting to a pressure source. In the embodiment shown in FIG. 1, these means are constituted by hollow pipe sockets 6, 7 to which may be connected a hose or a pipe. The purpose of this will be explained later.

Although the present detailed description of a preferred embodiment of the invention and the claims use the terms "approximately cylindrical" and "truncated cone" in connection with the various portions of the breast cup, it will be obvious to a person skilled in the art that the term "approximately cylindrical" may in the context of the invention also mean "conical". It is therefore conceivable that the portions 11, 12 and 4, 5, respectively, may together form a cone or a truncated cone without any distinct transition between the various portions.

In the embodiment of the outer part 1 shown in FIG. 1, the first portion 3 consist of a means 8 for connecting to a collecting device for the milk, e.g. a baby bottle or similar. The first portion 3 is further provided with means of connecting to a vacuum source, and in the embodiment shown, this is comprised of a hollow pipe socket 9 that can be connected to a hose or a pipe. The first portion 3 may also be provided with a dividing plate 10 (see FIG. 6) positioned so as to prevent the milk being sucked out through the pipe socket 9 when the device is in use. In the embodiment shown in FIG. 1, the first portion 3 is formed with an angle, but this portion may also be formed to be approximately straight.

Figure 3:
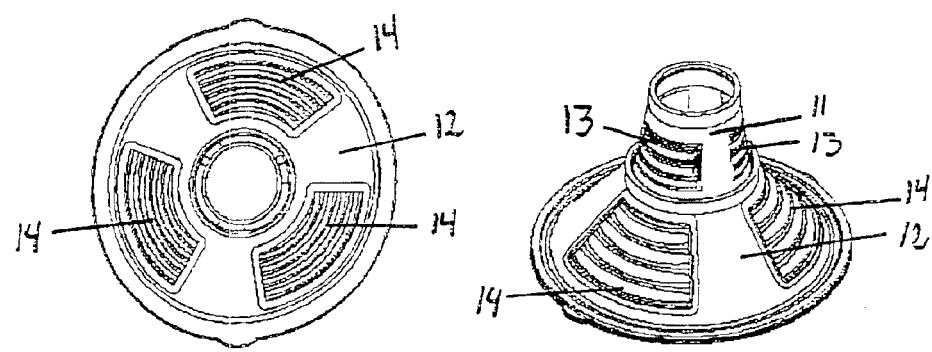
Figure 4:
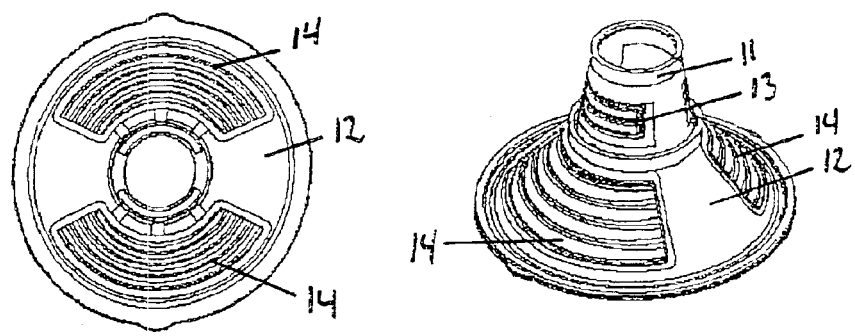

The inner part 2 of the breast cup in accordance with the invention is shown in FIG. 2. The inner part 2 consists of a first portion 11 with an approximately cylindrical shape and possibly a second portion 12, preferably in the form of a truncated cone. The first portion 11 consists of one or more areas in the form of membranes 13, and the second portion 12 is similarly provided with one or more areas in the form of membranes 14. FIGS. 3a–b and 4a–b illustrate two different versions of the inner part 2. FIG. 3 shows an embodiment in which the second portion 12 has three membranes 14, and FIG. 4 shows a version in which the second portion 12 of the inner part 2 has two membranes 14. In the embodiment of the inner part 2 shown in FIGS. 3 and 4, the membranes 14 are arranged symmetrically about the axis of the inner part 2. Similarly, the first portion 11 may be provided with one or more membranes 13.

Preferably, the outer part 1 and the inner part 2 are manufactured from a plastic material that tolerates autoclaving and/or cleaning with relatively strong cleaning agents. Furthermore, the inner part and the outer part must both be manufactured from a plastic material that can be welded or glued together. Polypropylene (PP) may be mentioned as an example of a suitable plastic material. The inner part and the outer part may also be manufactured from types of thermoplastic approved for foodstuffs and medical applications. The materials of the membranes 13, 14 must be flexible and able to withstand autoclaving and/or cleaning with relatively strong cleaning agents. Preferably, the membranes are manufactured from a thermoplastic elastomer. The materials of the outer/inner parts and the membranes must further be compatible, to allow them to be welded or glued together. It has proven advantageous for the membranes to be made corrugated or wave shaped, to allow them to be subjected to large movements.

A preferred method of manufacturing the breast cup in accordance with the invention will now be described with reference to FIGS. 5–7, which illustrate various steps in the manufacturing process.

The inner part 2 is first produced in a conventional manner, e.g. by injection moulding, giving the inner part an appearance such as shown in FIG. 5A. Then the membranes 13, 14 are moulded onto the inner part, as shown in FIG. 5B. The outer part 1 is produced in a conventional manner, e.g. by injection moulding. When the inner part 2 has been provided with membranes and the outer part is ready moulded, the inner part 2 and the outer part 1 must be joined to form a finished breast cup.

The joining of the outer part 1 and the inner part 2 takes place as shown in FIG. 6, by the circular portions of the outer part 1 and the inner part 2 indicated by arrows being heated by e.g. a heated plate, whereupon the inner part and the outer part are pressed together to weld the heated portions to each other, as shown in FIG. 7. FIGS. 7b–c show the welded areas in greater detail.

The outer part 1 and the inner part 2 now form a finished breast cup in accordance with the invention. Two cavities have now been formed; a first cavity 15 between the second portion 12 of the inner part 2 and the third portion 5 of the outer part 1, and a second cavity 16 between the first portion 11 of the inner part 2 and the second portion 4 of the outer part 1. Both these cavities 15, 16 communicate with the outside by means of the pipe sockets 6, 7.

By the above described embodiment of the breast cup in accordance with the invention, a total of three areas are provided which will be able to stimulate different parts of the breast. The first portion 11 of the inner part 2, wherein the nipple is located during use, forms the first stimulating area. A vacuum that pulls on the nipple, thereby simulating the suction from a breastfeeding child will constitute stimulation in this portion. The membranes 13, which will give a pulsating stimulus towards the base of the nipple, constitute the second stimulation area. This stimulus simulates the palate and tongue of a breastfeeding child. The third stimulation area is constituted by the membranes 14, which will give a pulsating stimulus towards an area located approximately 1.5–3.0 cm from the base of the nipple. This stimulus simulates the lips and jaw/palate of a breastfeeding child.

The breast cup in accordance with the invention is now ready for use, and the following will give a more detailed explanation of how the breast cup is used, with particular. reference to FIG. 8, which shows how the various parts of the breast cup is subjected to pressure and vacuum as a function of time. When the breast cup is to be used, the connecting means 9 is connected to the vacuum source, while the connecting means 6 and 7 are connected to separate pressure sources. The breast cup is also coupled to a collecting device. The breast cup may now be placed on the breast, and a pulsating vacuum of order of 50 mbar is applied to the first portion 3 for approximately 20 seconds, then going up further to approximately 100–150 mbar for the next 10 seconds. At the same time, a pulsating pressure of the order of 50 mbar to 450 mbar is applied to the first cavity 15, and then this pressure is reduced while pressurised fluid at a pressure of typically 300 mbar to 500 mbar is supplied to the other cavity 16. The pressures of the first and seconds cavities may be adjusted separately by the user only after approximately 30 seconds after the vacuum in the first portion 3 has been applied. As soon as the expulsion reflex has been initiated, the vacuum of the first portion may be reduced, and the pressure of the cavities is reduced maintained. Then the cycle is repeated, as shown in FIG. 7. The cycle time is adjustable, and will typically be variable within the range 1–4 seconds. In addition to being able to vary the cycle time, it is obviously also possible to adjust the pressure of the two cavities 15 and 16, as well as the vacuum in the first portion 3, independently of each other. This may for instance be done by using solenoid valves connected to an electronic controller, which also regulates the voltage of the pressure and vacuum pumps, thereby to change the flow. The pressure and the vacuum may be provided through air pumps/compressors or liquid pumps/compressors.

Figure 9:
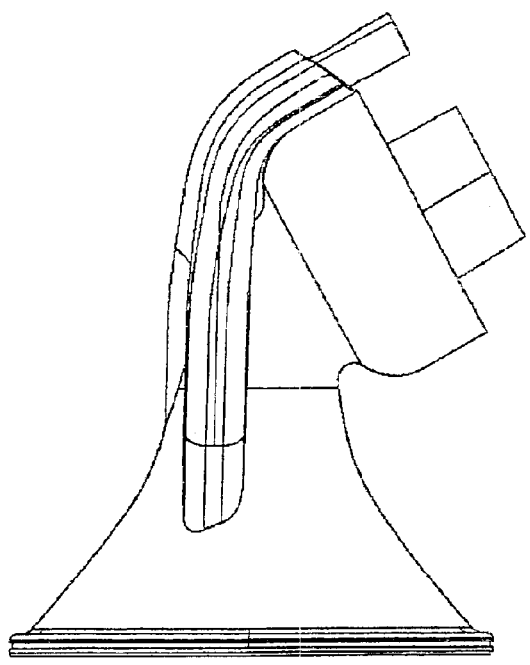
Figure 10:
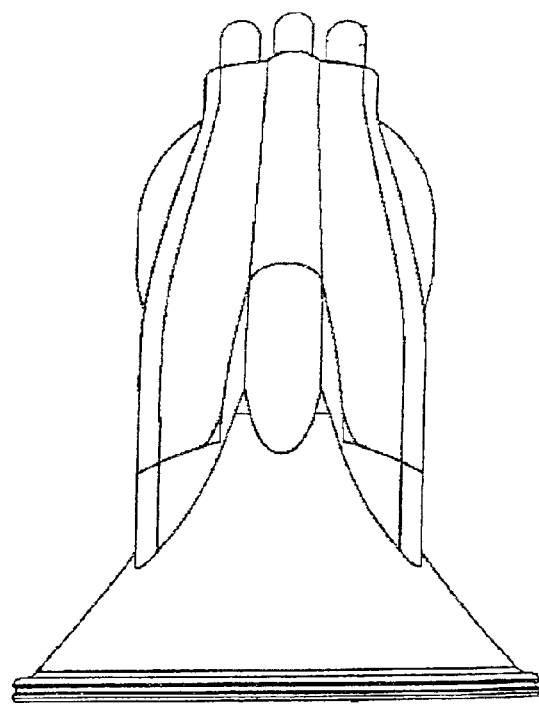

FIGS. 9 and 10 show a version of the breast cup in accordance with FIG. 1. What distinguishes this version from that of FIG. 1 is that the pipe sockets 6, 7, 9 for connecting the breast cup to pressure/vacuum sources in FIG. 1 have here been gathered together, to allow all connections to take place by means of e.g. a suitable adapter.

What is claimed is:

1. A breast cup for placing around a nipple and an areola area on a woman's breast, said breast cup being in the form of a truncated cone with a conical part and an approximately cylindrical part by the conical part of the cone, said cylindrical part of the breast cup forming first and second stimulating means that simulate the sucking and palate/tongue, respectively, of a breastfeeding child, and said conical part of the breast cup forming a third stimulating means that simulates the lips/jaws of a breastfeeding child, wherein the breast cup includes an outer part and an inner part, said inner part includes an approximately cylindrical portion with one or more areas provided with flexible membranes, and an approximately conical portion with one or more areas provided with flexible membranes, said outer part includes a generally conical portion shaped to be complementary to the conical portion of the inner part, and a generally cylindrical portion shaped to be complementary to the cylindrical portion of the inner part, and characterized in that said approximately conical portion of said inner part and said generally conical portion of said outer part define a first cavity, and said approximately cylindrical portion of said inner part and said generally cylindrical portion of said outer part define a second cavity.

2. A breast cup in accordance with claim 1, characterised in that the inner part or the outer part is provided with an additional portion in the form of an extension of the approximately cylindrical portion which additional portion is provided with connecting means for connecting the breast cup to a milk collecting device.

3. A breast cup in accordance with claim 1 or claim 2, characterised in that the outer part and the inner part are manufactured from a polymer material approved for medical use, optionally a thermoplastic.

4. A breast cup in accordance with claim 1 or 2, characterised in that the flexible membranes are manufactured from a polymer material approved for medical use, preferably a thermoplastic elastomer, which is compatible with the polymer material from which the inner part and the outer part are made.

5. The breast cup of claim 3, wherein said polymer material is thermoplastic polypropylene.

6. A method of pumping breast milk by use of a breast cup in accordance with claim 1 or 2, characterised in that the method includes the following steps:

a) connecting the first stimulating means to a vacuum source with adjustable pressure and frequency;

b) connecting the second and third stimulating means to one or more pressure sources with individually adjustable pressure and frequency, c) applying a pulsating vacuum of the order of 50 mbar to the first stimulating means for approximately 20 seconds, d) increasing the vacuum of point c) to 100–150 mbar for the next 10 seconds while at he same time applying a pulsating pressure of the order of 50 to 450 mbar to the second stimulating means, e) reducing the pressure of the second stimulating means while at the same time applying a pulsating pressure of the order of 300–500 mbar to the third stimulating means, f) reducing the vacuum of the first stimulating means, g) adjusting the pressure to the second and third stimulating means separately approximately 30 seconds after point c) has been carried out.

* * * * *